United States Patent
Barreca et al.

(10) Patent No.: US 10,597,353 B2
(45) Date of Patent: Mar. 24, 2020

(54) PROCESSES FOR THE PREPARATION OF DIASTEREOMERICALLY AND ENANTIOMERICALLY ENRICHED OXAZOLINES

(71) Applicant: QUÍMICA SINTÉTICA, S.A., Barcelona (ES)

(72) Inventors: Giuseppe Barreca, Montevecchia (IT); Marcello Rasparini, Mol (BE); Luca Carcone, Milan (IT); Fabio Morana, Novara (IT)

(73) Assignee: QUÍMICA SINTÉTICA, S.A., Barcelona (ES)

( * ) Notice: Subject to any disclaimer, the term of this patent is extended or adjusted under 35 U.S.C. 154(b) by 27 days.

(21) Appl. No.: 15/774,242

(22) PCT Filed: Nov. 10, 2016

(86) PCT No.: PCT/EP2016/077353
§ 371 (c)(1),
(2) Date: May 7, 2018

(87) PCT Pub. No.: WO2017/081206
PCT Pub. Date: May 18, 2017

(65) Prior Publication Data
US 2018/0327349 A1    Nov. 15, 2018

(30) Foreign Application Priority Data
Nov. 11, 2015 (EP) .................................. 15382562

(51) Int. Cl.
*C07C 227/32* (2006.01)
*C07C 269/06* (2006.01)
*C07C 269/04* (2006.01)
*C07C 229/36* (2006.01)
*C07C 253/20* (2006.01)
*C07C 255/21* (2006.01)

(52) U.S. Cl.
CPC .......... *C07C 227/32* (2013.01); *C07C 229/36* (2013.01); *C07C 253/20* (2013.01); *C07C 255/21* (2013.01); *C07C 269/04* (2013.01); *C07C 269/06* (2013.01); *C07B 2200/07* (2013.01)

(58) Field of Classification Search
None
See application file for complete search history.

(56) References Cited

U.S. PATENT DOCUMENTS

| 4,319,040 A | 3/1982 | Ohashi et al. |
| 4,480,109 A | 10/1984 | Ohashi et al. |

FOREIGN PATENT DOCUMENTS

| EP | 0112606 B1 | 3/1987 |
| EP | 0201039 B1 | 7/1991 |
| EP | 0375554 B1 | 5/1993 |

OTHER PUBLICATIONS

International Search Report and Written Opinion dated Feb. 6, 2017 for PCT Application No. PCT/EP2016/077353, 12 pages.
Cassani, Carlo, et al., "Synthesis of 9-amino(9-deoxy)epi cinchona alkaloids, general chiral organocatalysts for the stereoselective functionalization of carbonyl compounds", Nature Protocols (2013), Jan. 17, 2013, vol. 8, No. 2, pp. 325-344.
Green, Theodora W., "Protective Groups in Organic Synthesis", John Wiley & Sons (1999), pp. 266-272.
Green, Theodora W., "Protective Groups in Organic Synthesis", John Wiley & Sons (1999), pp. 503-550.
Okamoto, Masahiko, et al., "Direct stereochemical resolution of 3,4-dihydroxyphenylserine using a chiral crown ether stationary phase" Journal of Chromatography A 1994, vol. 675, pp. 244-247.
Sladojevich, Filippo, et al., "A new family of cinchona-derived amino phosphine precatalysts: Application to the highly Enantio- and Diastereoselective silver-catalyzed isocyanoacetate aldol reaction" Journal of the American Chemical Society 2011, Jan. 19, 2011, vol. 133, pp. 1710-1713.

*Primary Examiner* — Clinton A Brooks
*Assistant Examiner* — Jennifer C Sawyer
(74) *Attorney, Agent, or Firm* — Squire Patton Boggs (US) LLP

(57) ABSTRACT

The invention relates to an industrially viable and advantageous process for the preparation of (2S,3 R)-2-amino-3-(3,4-dihydroxyphenyl)-3-hydroxypropanoic acid, having the following formula (I) generally known as Droxidopa, or of intermediates useful in the synthesis thereof.

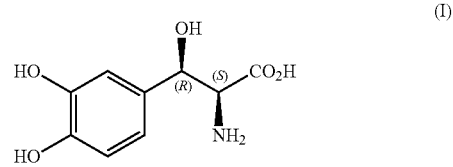

15 Claims, No Drawings

PROCESSES FOR THE PREPARATION OF DIASTEREOMERICALLY AND ENANTIOMERICALLY ENRICHED OXAZOLINES

This application claims the benefit of European Patent Application EP15382562.5 filed on Nov. 11, 2015.

FIELD OF THE INVENTION

The present invention relates to an industrially viable and advantageous process for the preparation of (2S,3R)-2-amino-3-(3,4-dihydroxyphenyl)-3-hydroxypropanoic acid, generally known as Droxidopa, or of intermediates useful in the synthesis thereof.

BACKGROUND ART (2S,3R)-2-amino-3-(3,4-dihydroxyphenyl)-3-hydroxypropanoic acid, also known as L-threo-dihydroxyphenylserine, L-threo-DOPS, L-DOPS or Droxidopa, is an orally active synthetic precursor of norepinephrine. Droxidopa replenishes depleted norepinephrine, allowing for re-uptake of norepinephrine into peripheral nervous system neurons. This reuptake, in turn, stimulates receptors for vasoconstriction, providing physiological improvement in symptomatic neurogenic orthostatic hypotension patients. It has also shown efficacy in other diseases, such as Parkinson's disease and depression.

Droxidopa has been used in Japan for many years for the treatment of orthostatic hypotension. It was originally approved in 1989 for the treatment of frozen gait or dizziness associated with Parkinson's disease and for the treatment of orthostatic hypotension, syncope or dizziness associated with Shy-Drager syndrome and familial amyloidotic polyneuropathy.

Marketing approval was later expanded to include treatment of vertigo, dizziness and weakness associated with orthostatic hypotension in hemodialysis patients.

Droxidopa has the following chemical structure:

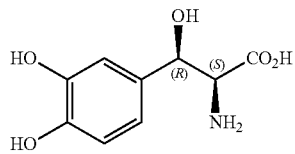

Its chemical preparation generally involves a multi-step synthesis. Typically, one or more of the necessary steps in the synthesis require that reactive sites, other than the site targeted for the reaction, are temporarily protected. Thus, the synthesis of Droxidopa typically comprises at least one protecting and associated deprotecting step. For example, the catechol moiety, the amine moiety, and/or the carboxyl moiety may require protection and subsequent deprotection, depending upon the synthetic route and the reagents used in the preparation of Droxidopa.

Several synthetic and enzymatic approaches to Droxidopa have been described in the literature.

Most of them entail the coupling between a conveniently protected 3,4-dihydroxy benzaldehyde with glycine to yield a diastereomerically enriched mixture of threo-DOPS. This approach, described by Microbiochemical Research Foundation in patent EP 0112606 B1, is not stereoselective and relies on fractional crystallizations to separate a threo/erythro mixture.

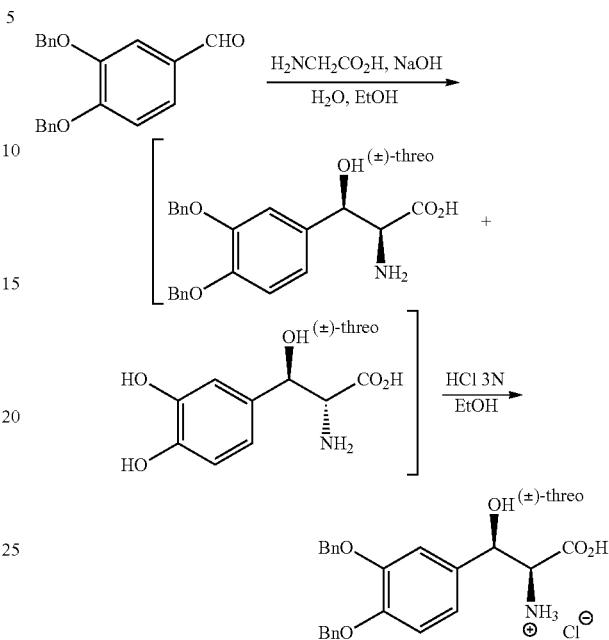

Suitable protecting groups for the hydroxyl moieties of 3,4-dihydroxy benzaldehyde are ethers (e.g. benzyl and methyl) or cyclic acetals (e.g. methylene acetal). The removal of cyclic acetals or methyl ethers requires treatment with a Lewis acid (e.g. $AlCl_3$) and a thiol (e.g. ethanethiol, a volatile compound with an extremely repulsive smell). To the contrary, the removal of benzyl ethers can be accomplished by simple, clean and quantitative hydrogenolysis.

The diastereomerically enriched mixture of the protected threo-DOPS can be converted into the optically active D- and L-threo-DOPS by optically resolving a racemic mixture of threo-2-(3,4-methylenedioxyphenyl)-N-carbobenzyloxyserine or threo-2-(3,4-dibenzyloxy-phenyl)-N-carbobenzyloxyserine, as detailed in U.S. Pat. Nos. 4,319,040 and 4,480,109, respectively. Following optical resolution of these racemic mixtures to give the desired L-enantiomer, the methylenedioxy or benzyl groups must be removed from the catechol moiety and the carbobenzyloxy (Cbz) group must be removed from the amine group to give Droxidopa.

According to an alternative approach described in patent EP 201039 B1, a racemic mixture of threo-2-(3,4-dibenzyloxy-phenyl)-N-acetylserine can be converted into L-threo-2-(3,4-dibenzyloxy-phenyl)-serine by treatment with a L-amino acylase.

A disadvantage associated with all the synthetic pathways cited above is that in converting a racemic starting material using an enantioselective enzyme or an optically active amine, a maximum yield of 50% of the enantiomerically pure end product can be reached.

An alternative procedure for the stereoselective preparation of Droxidopa has been described in patent EP 375554 B1. According to the latter, the two stereocenters are introduced simultaneously with a Noyori-type asymmetric hydrogenation with dynamic kinetic resolution (AH-DKR). The process is particularly interesting because it is catalyzed by the cheapest of the transition metals (ruthenium) and of the chiral phosphines (Binap) employed in asymmetric hydrogenations. However the proposed conditions are not suitable for an industrial production of Droxidopa, because: 100 bar of hydrogen pressure is out of reach in normal industrial vessels; the reported reaction time is unpractical (almost 1 week); the best solvent is dichlorometane (which should be avoided for environmental concerns); and the deprotection of the methylenedioxy moiety requires large excesses of $AlCl_3$ or $AlBr_3$.

A stereoselective enzymatic approach to Droxidopa has been described in patent JP 5028850 and entails the coupling of glycine or a salt thereof with 3,4-dihydroxybenzaldehyde in the presence of a threonine aldolase to form the corresponding enantiomerically enriched amino acid derivative.

An innovative synthetic approach for the preparation of diastereomerically and enantiomerically enriched oxazolines (A) (by reaction of isocyanoacetates with aldehydes in the presence of 9-amino(9-deoxy)epi Cinchona alkaloid derivatives and a salt of silver or gold) has been described in the *Journal of the American Chemical Society* (2011), 133, 1710-1713.

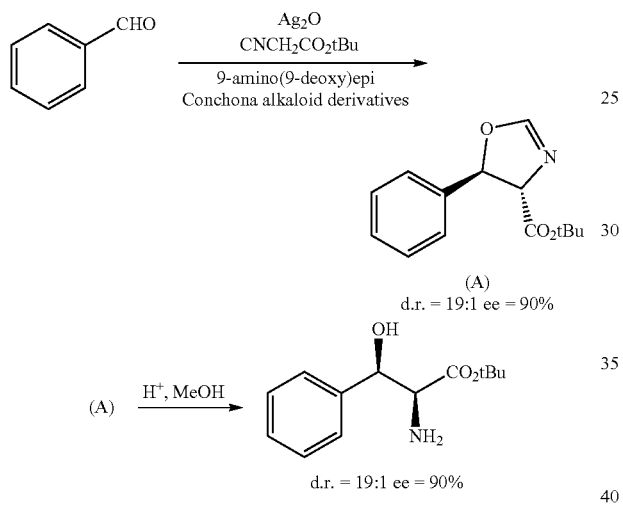

Said oxazolines (A) can be further converted into the corresponding tert-butyl esters by hydrolysis.

Aim of this invention is to provide a chemical method to prepare Droxidopa or intermediates useful in the synthesis thereof, characterized by high yields and levels of stereocontrol avoiding the use of dangerous reagents and providing the desired compounds with a purity appropriate for the use in pharmaceuticals.

SUMMARY OF THE INVENTION

These objectives were achieved with the present invention which, in a first aspect thereof, relates to a process for the preparation of a diastereomerically and enantiomerically enriched mixture of an amino acid of general formula (IV) or a salt thereof:

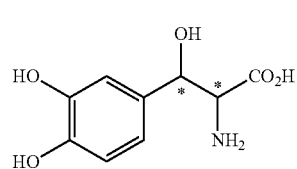

said process comprising the following synthetic operations:

a) preparing a diastereomerically and enantiomerically enriched mixture of the oxazoline of general formula (II) by reacting a benzaldehyde (I) with an isocyanoacetate (V) in the presence of a catalytic system comprising a 9-amino(9-deoxy)epi Cinchona alkaloid derivative (VIII) and a salt of silver or gold or a mixture thereof:

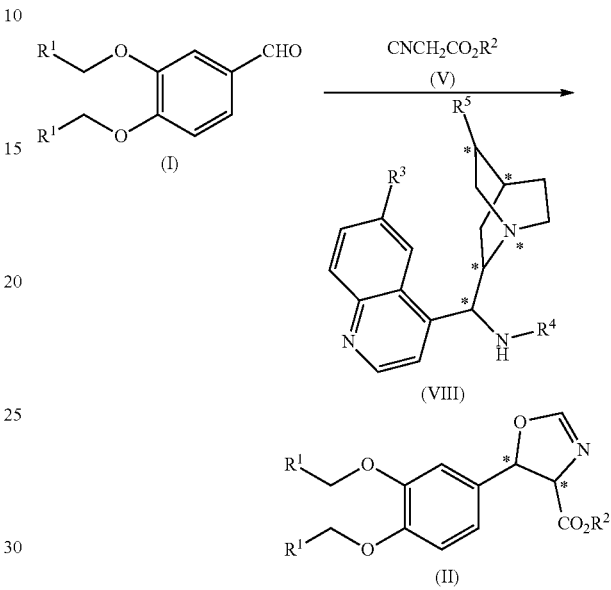

wherein $R^1$ is a C6-C10 aryl or a substituted C6-C10 aryl (e.g. phenyl);

$R^2$ is a C1-C6 linear or branched alkyl (e.g. methyl, ethyl, n-propyl, iso-propyl, n-butyl, iso-butyl or tert-butyl), a C6-C10 aryl (e.g. phenyl) or a C1-06 linear or branched alkyl substituted with a C6-C10 aryl (e.g. benzyl);

$R^3$ is H, OH, or a C1-C6 linear or branched alkoxy (e.g. methoxy);

$R^4$ is

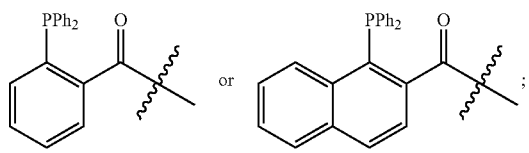

and $R^5$ is an ethyl or a vinyl group;

b) converting said enriched mixture of the oxazoline of general formula (II) into a diastereomerically and enantiomerically enriched mixture of the protected amino acid of general formula (III):

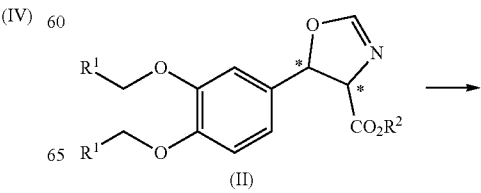

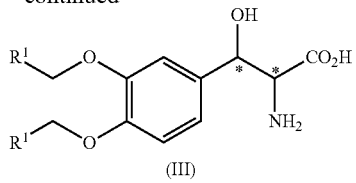

c) converting the enriched mixture of the protected amino acid of general formula (III) into a diastereomerically and enantiomerically pure mixture of the amino acid of general formula (IV):

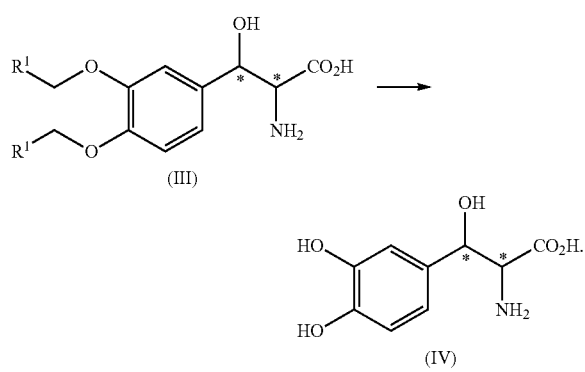

DETAILED DESCRIPTION OF THE INVENTION

All terms used in the present application, unless otherwise indicated, must be interpreted in their ordinary meaning as known in the technical field. Other more specific definitions for some terms used in the present application are given below and are intended to be applied uniformly to the entire description and claims, unless otherwise indicated.

In general, the nomenclature used in this Application is based on AUTONOM™ v.4.0, a Beilstein Institute computerized system for the generation of IUPAC systematic nomenclature. If there is a discrepancy between a depicted structure and a name given to that structure, the depicted structure should be considered correct. Furthermore, if the stereochemistry of a structure or a portion of a structure is not indicated with, for example, bold or dashed lines, the structure or portion of the structure has to be interpreted as encompassing all existing stereoisomers of it.

The compounds prepared by the processes of the present invention may have one or more stereogenic centers and may exist and may be used or isolated in enantiomerically pure forms, as enantiomeric enriched mixtures as well as in diastereomerically pure forms or as diastereomeric enriched mixtures. It is to be understood that the processes of the present invention can give rise to any of the previous forms or a combination thereof. It is to be further understood that the products of the processes described herein, can be isolated as enantiomerically and diastereomerically pure forms or as enantiomerically and diastereomerically enriched mixtures.

The sign "*" (asterisk) present in some formulae of this description indicates stereogenic (asymmetric) center, although the absence of asterisks does not necessarily imply that the compound lacks a stereocenter. Such formulae may refer to the racemate or to individual enantiomers or diastereomers, which may or may not be substantially pure.

A mixture of (R,S) enantiomers can contain the two single enantiomers in any ratio to each other. The enantiomeric purity is generally expressed as "enantiomeric excess" or ee and is defined, for example for the (S) enantiomer, as [(S−R)/(R+S)]×100, wherein S and R are respectively the amounts of the (S) and (R) enantiomers (as determined for example by GC or HPLC on a chiral stationary phase or polarimetry).

The term "aryl" refers to any substituent derived from a monocyclic or a polycyclic aromatic hydrocarbon by removal of a hydrogen atom from a ring carbon atom (i.e. phenyl, tolyl, 1-naphtyl or 2-napthyl).

The term "racemic" refers to a sample of a chiral compound which contains both the (+) and (−) isomers in equal amount.

The term "enantiomerically enriched" as used herein means that one of the enantiomers of a compound is present in excess compared to the other enantiomer.

The term "enantiomerically pure" as used herein means that the enantiomeric purity is usually at least about 96%, preferably at least 99%, more preferably at least 99.5%.

The term "diastereomerically enriched" as used herein means that one of the diastereomers of a compound is present in excess compared to the other diastereomer.

The term "diastereomerically pure" as used herein means that the diastereomeric purity is usually at least about 96%, preferably at least 99%, more preferably at least 99.5%.

The symbol  (dashed bond) present in some of the formulae of the description and the claims indicates that the substituent is directed below the plane of the sheet.

The symbol ──■ (wedge bond) present in some of the formulae of the description and the claims indicates that the substituent is directed above the plane of the sheet.

The compounds obtained by the chemical transformations of the present invention can be used for the following steps without further purification or can be separated and purified by employing conventional methods well known to those skilled in the art, such as recrystallization, column chromatography, or by transforming them into a salt or in a co-crystal with an appropriate co-former, or by washing with an organic solvent or with an aqueous solution, optionally adjusting pH.

It will be understood that any compound described herein may also describe any salts or co-crystals thereof.

The term "seed" refers to a crystalline substance that is added to a solution of the same substance to induce its crystallization. Seeding with a specific optical isomer often has the useful effect of promoting crystallization of the substance in the same form of the seed.

It should be noted that, during the conversion of the diastereomerically and enantiomerically enriched mixture of the oxazoline of general formula (II) into the enriched mixture of the amino acid of general formula (IV), neither epimerization (i.e. loss of diastereoselectivity towards the erythro isomer) nor racemization (conversion of the major enantiomer towards the minor leading to a lower ee) are observed. Accordingly, the d.r. (diastereomeric ratio, namely the ratio of the percentage of one diastereoisomer in a mixture to that of the other diastereoisomer) and the ee detected in the enriched mixture of the oxazoline of general formula (II) are retained unchanged in the enriched mixture of the amino acid of general formula (IV).

According to its most general aspect, the present invention relates to a process for the preparation of a diastereomerically and enantiomerically enriched mixture of an amino acid of general formula (IV) or salts thereof.

The first operation of the process of the invention, a), consists in the preparation of a diastereomerically and enantiomerically enriched mixture of the oxazoline of general formula (II) by means of an aldol reaction, in which a benzaldehyde (I) is reacted with an isocyanoacetate (V) in the presence of a catalytic system comprising a 9-amino(9-deoxy)epi Cinchona alkaloid derivative (VIII) and a salt of silver or gold or a mixture thereof.

The benzaldehydes (I) and the isocyanoacetates (V) used as reagents in this operation are commercially available; alternatively, they can be prepared according to standard techniques in organic synthesis; in particular, the isocyanoacetates (V) can be prepared according to operation d) described below.

Said aldol reaction is normally carried out at temperatures between −40 and 80° C., preferably between −20 and 60° C., for example between 10 and 30° C., in an aprotic polar solvent, such as an ether (preferably tetrahydrofuran, 2-methyltetrahydrofuran, methyl-tert-butyl ether or cyclopentylmethyl ether), an acetate (preferably ethyl acetate or iso-propylacetate), acetonitrile, a chlorinated solvent (such as dichloromethane) or a mixture thereof.

Salts of silver or gold suitable for the aim are for example silver acetate, silver carbonate, silver oxide, chloro(triphenylphosphine)gold or a mixture thereof.

Cinchona alkaloid derivatives (VIII) useful for the invention can be prepared according to the procedure described in *Nature Protocols* (2013), 8, 325-344 and *Journal of the American Chemical Society* (2011), 133, 1710-1713 starting from the commercially available cinchonidine, cinchonine, quinine or quinidine (usually sold as a mixture of the unsaturated/saturated derivatives).

According to an alternative embodiment of the process object of the most general aspect of the present invention, said unsaturated/saturated mixture is converted into a mixture of unsaturated/saturated 9-amino(9-deoxy)epi Cinchona alkaloid derivatives which is used as such in the aldol reaction of operation a).

Preferably the 9-amino(9-deoxy)epi Cinchona alkaloid derivative (VIII) used in operation a) is characterized by general formula (VIIIA) or (VIIIB):

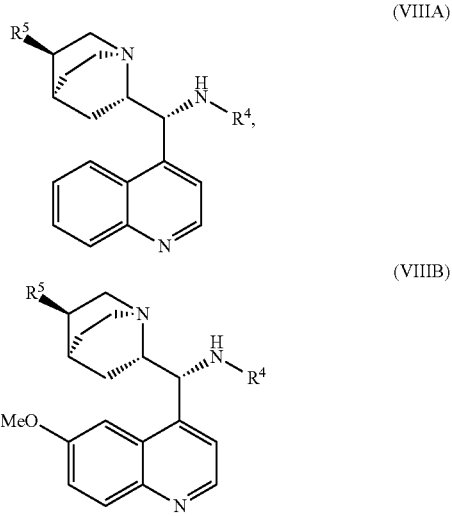

wherein R4 and R5 have the meanings given above.

The amount of isocyanoacetate (V) is normally between 1 and 1.5 equivalents, preferably between 1.05 and 1.1 equivalents, with respect to the amount of benzaldehyde (I) used.

The molar amount of the 9-amino(9-deoxy)epi Cinchona alkaloid derivative is normally between 1/200 and 1/20 with respect to the amount of benzaldehyde of general formula (I) used, for example between 1/100 and 1/50.

The molar amount of the salt of silver or gold or of the mixture thereof with respect to the 9-amino(9-deoxy)epi Cinchona alkaloid derivative in the catalytic system is normally between 1:1 and 1:8 (mol/mol).

The isocyanoacetates (V) for use in operation a) can be prepared in an operation d), comprising the following steps:

d.1) converting a glycine derivative of formula (VI) or a salt thereof into the corresponding N-formyl derivative (VII):

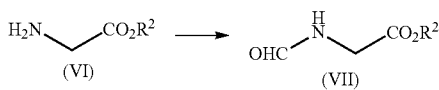

d.2) dehydrating said N-formyl derivative (VII) to obtain an isocyanoacetate (V):

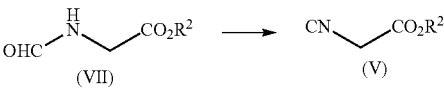

wherein $R^2$ is a C1-C6 linear or branched alkyl (e.g. methyl, ethyl, n-propyl, iso-propyl, n-butyl, iso-butyl, tert-butyl), a C6-C10 aryl (e.g. phenyl), or a C1-C6 linear or branched alkyl substituted with a C6-C10 aryl (e.g. benzyl).

Step d.1) includes the treatment of a glycine derivative of formula (VI) or a salt thereof (preferably the hydrochloride salt) with a formate, preferably ethyl formate, to obtain a N-formyl derivative (VII). When a salt of the glycine derivative of formula (VI) is used as the starting compound, the conditions set out above further require the presence of an organic base, such as a tertiary amine, e.g. triethylamine, N,N-diisopropylethylamine, N,N-diisopropylmethylamine, N-methylmorpholine or N,N-dicyclohexylmethylamine. The amount of formate is normally between 5 and 15 equivalents, preferably between 8 and 10 equivalents, with respect to the amount of glycine derivative (VI) used.

The amount of organic base is normally between 1 and 1.5 equivalents, preferably is 1.1 equivalents, with respect to the amount of the salt of glycine derivative (VI) used.

Step d.2) entails the conversion of the N-formyl derivative (VII), optionally isolated, into an isocyanoacetate (V) by treatment with one of the dehydrating agents generally known in the field, such as, for example:

Bis(trichloromethyl) carbonate (triphosgene) or trichloromethyl chloroformate (diphosgene) in the presence of a base, such as one of the tertiary amine listed above to perform step d.1);

$POCl_3$ in the presence of a base, such as one of the tertiary amine listed above to perform step d.1);

Tosyl chloride in the presence of a base, such as one of the tertiary amine listed above to perform step d.1);

Mesyl chloride in the presence of a base, such as one of the tertiary amine listed above to perform step d.1);

The Burgess reagent.

Preferably step d.2) is performed by treatment with $POCl_3$ and triethylamine or N,N-diisopropylethylamine in a suitable solvent (preferably a chlorinated solvent, for example dichloromethane).

The amount of $POCl_3$ is normally between 1 and 1.2 equivalents, preferably between 1.05 and 1.1 equivalents, with respect to the amount of N-formyl derivative (VII) used.

Suitable amounts of triethylamine or N,N-diisopropylethylamine are normally between 2 and 5 equivalents, preferably between 2.2 and 2.5 equivalents, with respect to the amount of N-formyl derivative (VII) used.

According to an even more preferred embodiment of the present invention, the solution resulting from step d.2), containing the isocyanoacetate (V), is used as such in the aldol reaction of operation a).

Operation b) of the process of the invention comprises the conversion of the diastereomerically and enantiomerically enriched mixture of the oxazoline of general formula (II), obtained in operation a), into a diastereomerically and enantiomerically enriched mixture of the protected amino acid of general formula (III). This operation includes the following steps:

b.1) converting the enriched mixture of the oxazoline of general formula (II) into the corresponding enriched mixture of N-formyl derivative (IX):

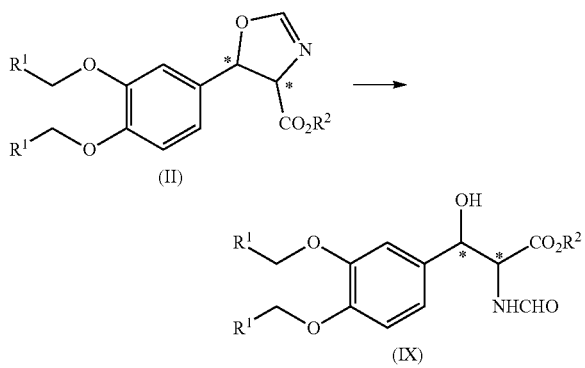

b.2) converting the enriched mixture of N-formyl derivative (IX) into a diastereomerically and enantiomerically enriched mixture of the protected amino acid of general formula (III):

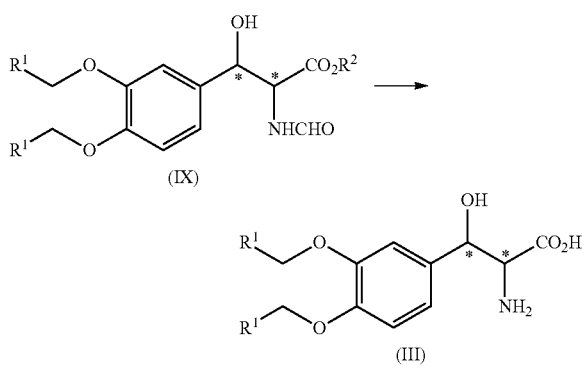

wherein $R^1$ and $R^2$ have the meanings given above.

The transformation object of step b.1) entails the conversion of the diastereomerically and enantiomerically enriched mixture of the oxazoline of general formula (II), optionally isolated, into the corresponding enriched mixture of N-formyl derivative (IX) using one of the methods generally known in the field, for example by treatment with an acid. Suitable conditions comprise, for example, the use of a 5% aqueous solution of citric acid.

The enriched mixture of N-formyl derivative (IX) thus obtained, optionally isolated, is further subjected, according to step b.2), to acid hydrolysis to yield a diastereomerically and enantiomerically enriched mixture of the protected amino acid of general formula (III). Acid conditions useful for the purpose are generally known in the field and include for example the treatment with hydrochloric acid or a solution of hydrogen chloride in a suitable organic solvent, such as an alcohol (e.g. methanol).

In the case when $R^2$ forms, together with the carboxyl group to which it is attached, an ester group not hydrolysable under acid conditions, for example a methyl, ethyl, n-propyl, iso-propyl, n-butyl, iso-butyl, phenyl or benzyl ester, the acid hydrolysis produces a N-deformylated compound of formula (X) below:

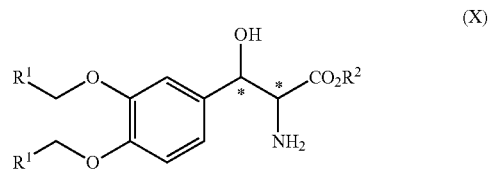

In this case, step b.2) further includes the hydrolysis of the ester moiety with one of the methods known to the skilled person. Preferably, said hydrolysis is carried out by contacting the enriched mixture of N-formyl derivative (IX) or the corresponding N-deformylated compound of formula (X) with a hydroxide or a carbonate of an alkaline metal (such as $K_2CO_3$, $Na_2CO_3$, $Li_2CO_3$, $Cs_2CO_3$, KOH, NaOH, LiOH) in a water miscible solvent (e.g. methanol, ethanol, tetrahydrofuran, dioxane or a mixture thereof) in the presence of water. The amount of the hydroxide or carbonate of the alkaline metal used is normally between 1 and 5 equivalents, preferably 3 equivalents, compared to the molar quantity of either the N-formyl derivative (IX) or the compound of formula (X) used.

The following operation of the process of the invention, c), entails the conversion of the diastereomerically and enantiomerically enriched mixture of the protected amino acid of general formula (III), optionally isolated, into the diastereomerically and enantiomerically pure mixture of the amino acid of general formula (IV). This operation can be performed according to two alternative routes of synthesis c.i) and c.ii).

The synthetic scheme c.i) includes the following steps:

c.i.1) converting the enriched mixture of the protected amino acid of general formula (III) into a diastereomerically and enantiomerically enriched mixture of the amino acid of general formula (IV):

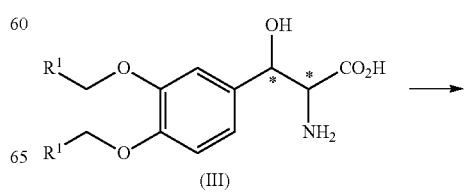

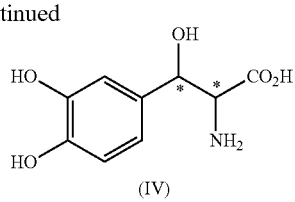

(IV)

wherein R[1] has the meanings given above.

c.i.2) converting the enriched mixture of the amino acid of general formula (IV) into a diastereomerically and enantiomerically pure mixture thereof.

Step c.i.1) includes the de-protection of the catechol moiety of the diastereomerically and enantiomerically enriched mixture of the protected amino acid of general formula (III). This step can be performed using one of the methods known to the person skilled in the art, for example one of those described in Theodora W. Green, *Protective Groups in Organic Synthesis*, John Wiley & Sons (1999), pages 266-272, which are herein incorporated by reference. For example, this step can be carried out by treatment with hydrogen in the presence of a catalyst (e.g. palladium, platinum or nickel) optionally supported on an appropriate carrier, such as carbon or barium carbonate in an alcohol (preferably methanol or ethanol) or an aqueous mixture thereof. In order to promote the hydrogenolysis or to improve the solubility of the reaction product, an appropriate acid may be added to the reaction mixture, preferably in a ratio of 0.8 to 2.0 moles to 1.0 mole of the diastereomerically and enantiomerically enriched mixture of the protected amino acid of general formula (III). Acids useful for the aim are mineral acids (e.g. hydrochloric acid or sulfuric acid) or organic acids (such as acetic acid or methanesulfonic acid).

Step c.i.2) entails the conversion of the diastereomerically and enantiomerically enriched mixture of the amino acid of general formula (IV) or a salt thereof (preferably the hydrochloride salt) into a diastereomerically and enantiomerically pure mixture thereof by crystallization of a supersaturated solution of said enriched mixture (IV) in water or in a mixture comprising water and a water-miscible solvent, such as an alcohol (preferably methanol or ethanol), a ketone (preferably acetone) or an ether (preferably dioxane or tetrahydrofuran). The volume of the solvent is normally between 50 mL and 80 mL per gram of the diastereomerically and enantiomerically enriched mixture of the amino acid of general formula (IV) used; even more preferably, said volume is between 60 and 70 mL per gram of said diastereomerically and enantiomerically enriched mixture.

In a possible variant of this operation, a seed of the desired optically active isomer is added to the supersaturated solution before cooling it down. The supersaturated solution of said diastereomerically and enantiomerically enriched mixture may optionally contain an organic base, such as dimethylaniline, dimethylbenzylamine or triethylamine; an inorganic base, such as sodium hydroxide or potassium hydroxide; an inorganic acid, such as hydrochloric acid or sulfuric acid; an organic acid such as para-toluenesulfonic acid, methanesulfonic acid, oxalic acid or ascorbic acid; or an amino acid such as D-, L- and D,L-aspartic acid or D-, L- and D,L-glutamic acid. When used, these bases, acids or amino acids are present in an amount of 0.05 to 0.6 mole per mole of the diastereomerically and enantiomerically enriched mixture of the amino acid of general formula (IV), to thereby suppress the crystallization of the undesired isomer and, hence, increase the stability of the supersaturated solution.

The alternative synthetic scheme c.ii) includes the following steps:

c.ii.1) protecting the amino group of the diastereomerically and enantiomerically enriched mixture of the protected amino acid of general formula (III), producing an enriched mixture of the protected amino acid of general formula (XI):

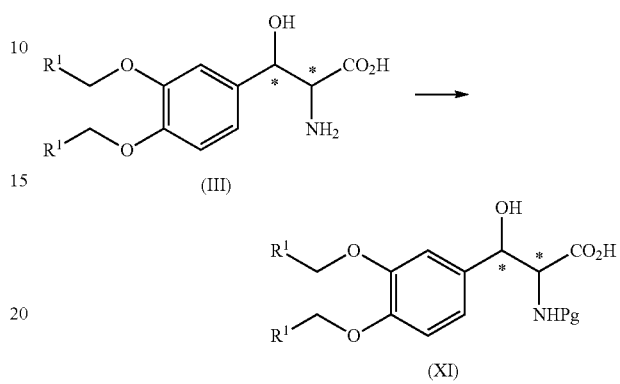

c.ii.2) converting said enriched mixture of the protected amino acid of general formula (XI) into a diastereomerically and enantiomerically pure mixture of the protected amino acid of general formula (XII):

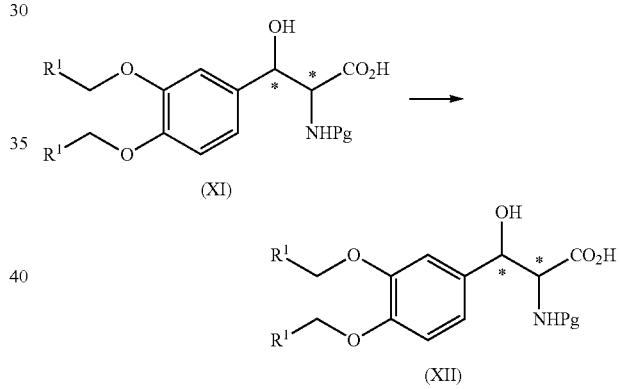

c.ii.3) converting the pure mixture of the protected amino acid of general formula (XII) into a diastereomerically and enantiomerically pure mixture of the amino acid of general formula (IV):

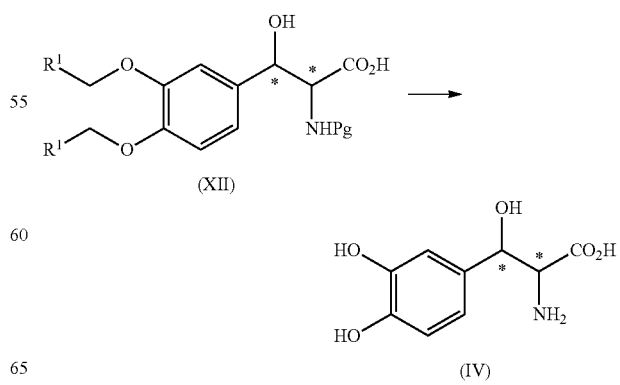

wherein:

R¹ has the meanings given above; and

Pg is a nitrogen protecting group, such as tert-butyloxycarbonyl (Boc) and benzyloxycarbonyl (Cbz).

Step c.ii.1) includes the protection of the amino group of the diastereomerically and enantiomerically enriched mixture of the protected amino acid of general formula (III), optionally isolated, according to one of the procedures described in Theodora W. Green, *Protective Groups in Organic Synthesis*, John Wiley & Sons (1999), pages 503-550, which are herein incorporated by reference. Preferably this step is performed by treating mixture (III) with di-tert-butyldicarbonate ($Boc_2O$), benzyl chloroformate (CbzCl), N-(benzyloxycarbonyloxy)succinimide (Cbz-OSu) or dibenzyl dicarbonate ($Cbz_2O$) in an aprotic polar solvent, such as dimethylacetamide, dimethylformamide, N-methylpyrrolidone, tetrahydrofuran, acetonitrile, ethyl acetate, or in a chlorinated solvent, such as dichloromethane, or a mixture thereof, optionally in the presence of a tertiary amine.

The following step c.ii.2) entails the conversion of the enriched mixture of the protected amino acid of general formula (XI), optionally isolated, into a diastereomerically and enantiomerically pure mixture thereof, (XII), by treatment with an optically active amine (such as (S)-2-amino-1,1-diphenylpropanol) to obtain the corresponding salt, followed by diastereomeric salt resolution of the two enantiomers of the threo product and de-blocking of the diastereomerically and enantiomerically pure mixture by treatment with an acid.

The formation and fractionation of the amine salt are generally performed by heating to a temperature next to the boiling point of the used solvent, followed by cooling to a temperature between 0 and 30° C. The formation of the amine salt is complete within some minutes but the reaction time can be extended to several hours without causing any disturbance. The molar ratio of the optically active amine with respect to the diastereomerically and enantiomerically enriched mixture of the protected amino acid of general formula (XI) is from 0.65 to 1. Examples of solvents suitable for the formation and fractionation of the amine salts are alcohols (e.g. methanol, ethanol and iso-propyl alcohol), ethers (such as tetrahydrofuran and dioxane), acetonitrile, water and mixtures thereof.

In a possible variant of the process, between steps c.ii.2) and c.ii.3) an additional step, c.ii.2'), is carried out, in which the salt with the optically active amine is slurried in an acetate (preferably iso-propyl acetate), in acetonitrile or a mixture thereof, to reduce the amount of residual impurities.

Acid suitable to decompose the salt are mineral acids such as hydrochloric acid, sulfuric acid and phosphoric acid. The acid is generally used in amounts between 1 and 10 moles per mole of amine salt.

The final step, c.ii.3), entails the conversion of the diastereomerically and enantiomerically pure mixture of the protected amino acid of general formula (XII) into a diastereomerically and enantiomerically pure mixture of the amino acid of general formula (IV). This operation can be performed using one of the methods known to the skilled person for example one of those described in Theodora W. Green, *Protective Groups in Organic Synthesis*, John Wiley & Sons (1999), pages 503-550, which are herein incorporated by reference. Preferably, when Pg is benzyloxycarbonyl, said de-protection is performed according to one of the methods described to operate step c.i.1). When Pg is tert-butyloxycarbonyl, it can be carried out by treating with phosphoric acid, trifluoroacetic acid (TFA), a solution of hydrogen chloride in water or in an organic solvent, or by treatment with formic acid.

Preferably the diastereomerically and enantiomerically enriched mixture of the oxazoline of general formula (II) prepared in operation a) of the process, is an enantiomerically enriched trans-oxazoline of general formula (IIA):

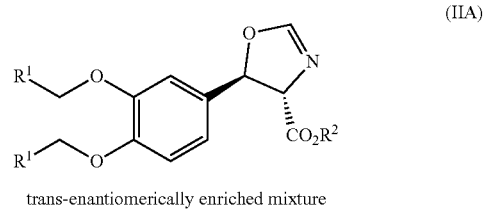

(IIA)

trans-enantiomerically enriched mixture

Compound IIA is obtained by carrying out the process as defined above wherein the 9-amino(9-deoxy)epi Cinchona alkaloid derivative (VIII) used in operation a) is characterized by general formula (VIIIC)

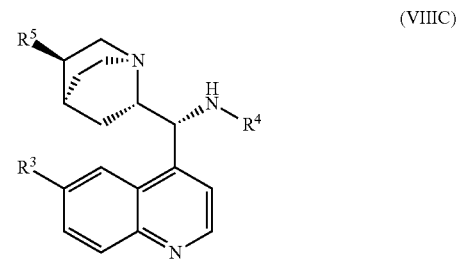

(VIIIC)

wherein $R^3$, $R^4$ and $R^5$ are as defined above. In this case, the process leads to the formation of an enantiomerically pure threo-amino acid of general formula (IVA):

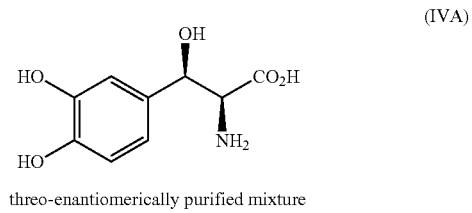

(IVA)

threo-enantiomerically purified mixture

Particularly, the 9-amino(9-deoxy)epi Cinchona alkaloid derivative of formula (VIIIC) used in operation a) is characterized by general formula (VIIIA) or (VIIIB) as defined above.

The diastereomerically and enantiomerically pure mixture of the amino acid of general formula (IV) obtained by the processes object of the present invention can be converted in a salt or a co-crystal thereof in a further optional step.

When the pure mixture of the amino acid of general formula (IV), or any other of the compounds described in the present application, are obtained with a degree of chemical purity not suitable for the inclusion in a medicament, the process object of the present invention entails a further step of purification, for example by means of chromatography or crystallization, optionally after formation of an addition compound, such as for example a salt or a co-crystal, or by washing with an organic solvent or an aqueous solution, optionally adjusting the pH.

The invention will be further illustrated by the following examples.

Example 1

Preparation of (2S,3R)-2-amino-3-(3,4-bis(benzyloxy)phenyl)-3-hydroxypropanoic Acid, Compound of Formula (III) wherein $R^1$ is Phenyl This example is representative of operations a) and b) of the process of the invention.

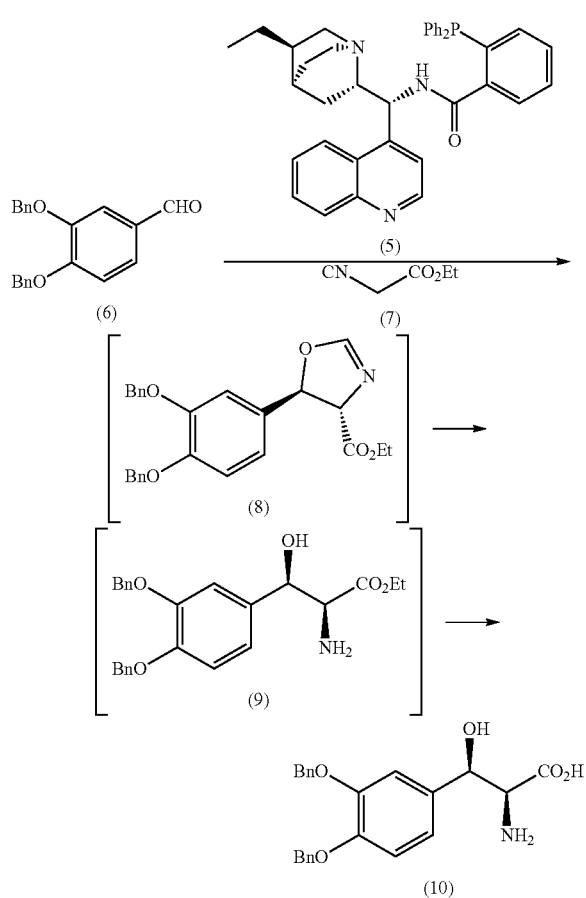

A 10 mL test tube was charged with 3,4-dibenzyloxybenzaldehyde 6 (0.271 g, 0.85 mmol) and compound 5 (0.010 g, 2 mol %). Iso-propyl acetate was added (2.8 mL) followed after 10 min by Ag$_2$O (0.001 g, 0.5 mol %). The mixture was stirred at 20° C. for 20 minutes, then ethyl isocyanoacetate 7 (0.101 g, 0.89 mmol) was added dropwise. The reaction was stirred at 20° C. for 1.5 hours monitoring periodically by TLC (AcOEt/Hexane 4:6, UV and molibdic) until disappearance of the aldehyde 6.

The mixture was filtered on a HPLC filter and the filtrate concentrated to a residue. Crude oxazoline 8 (0.85 mmol theoretical) was dissolved in THF (3.7 mL) and 6N HCl (0.38 mL, 2.30 mmol). The mixture was stirred at 50° C. for 2 hours, monitoring periodically by TLC (AcOEt/Hexane 4:6 and 100% AcOEt, UV and molibdic) until disappearance of the oxazoline 8 and of the corresponding N-formyl compound.

When the conversion was complete, the mixture was cooled to 0° C. and 2N NaOH (2.8 mL, 5.64 mm) was added dropwise monitoring that the internal temperature did not exceed 10° C. The mixture was then warmed to 25° C. and stirred at this temperature overnight. The pH was adjusted to 5 by addition of acetic acid whereupon precipitation of the amino acid occurred. The mixture was heated to 50° C. in order to observe a clear separation of the phases; the organic layer was separated and used as such in the following Example.

Example 2

Preparation of (2S,3R)-2-amino-3-(3,4-bis(benzyloxy)phenyl)-3-hydroxypropanoic Acid, Compound of Formula (XI) wherein $R^1$ is Phenyl and Pg is benzyloxycarbonyl This example is representative of step c.ii.1) of the process of the invention.

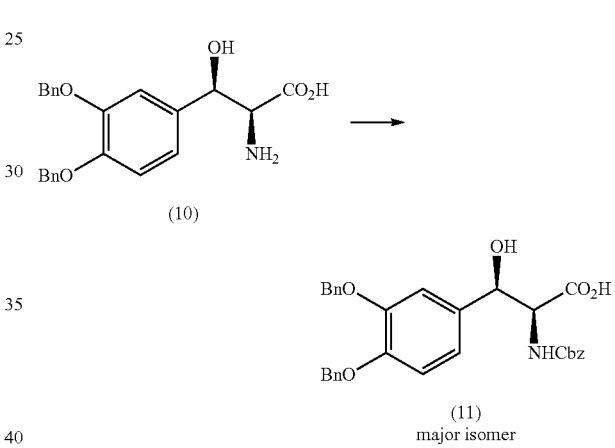

major isomer

To the organic layer prepared as described in Example 1 (0.85 mmol theoretical), ethyl diisopropylamine was added (0.223 mL, 1.28 mmol) at 0° C. followed by Cbz-OSu (0.234 g, 0.94 mmol) and the reaction was stirred at 25° C. for 1 hour. When the reaction was complete, pH was adjusted to about 5 by addition of a mixture of acetic acid (0.1 mL) and water (1.0 mL). THF was removed under reduced pressure and the product extracted with iso-propyl acetate. The combined organic layers were washed with water and concentrated to a residue.

An aliquot of the residue was converted into Droxidopa as described in example 4 and analysed by HPLC according to the method described in the *Journal of Chromatography A* 1994; 675: 244-247 showing a diastereomeric ratio of 90:10 and an enantiomeric ratio 85:15 (ee=70%).

Example 3

Purification of the isomers mixture of (2S,3R)-2-amino-3-(3,4-bis(benzyloxy)phenyl)-3-hydroxypropanoic acid, compound of formula (XI) wherein $R^1$ is phenyl and Pg is benzyloxycarbonyl. This example is representative of step c.ii.2) of the process of the invention.

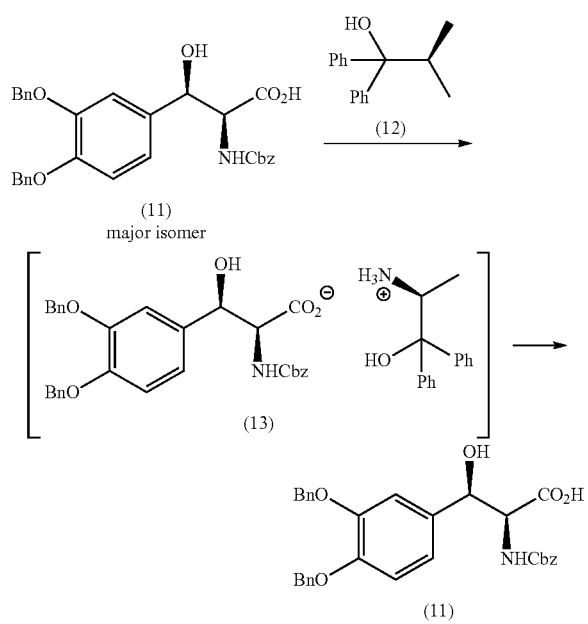

(11) major isomer (13)

(11)

To the crude acid 11 prepared as described in example 2 (11.8 mmol theoretical) and dissolved in iso-propyl acetate (70 mL), (S)-2-amino-1,1-diphenylpropan-1-ol (2.68 g, 11.8 mmol) was added. The mixture was heated to reflux until a solution was obtained.

The mixture was cooled to 25° C., heated to 60° C. for 1 hour, cooled to 0° C. over 2 hours and stirred at the same temperature for 1 hour. The solid was filtered, washed with iso-propyl acetate and dried under reduced pressure at 50° C. obtaining 5.7 g of salt 13 (64% yield over 3,4-dibenzyloxy benzaldehyde 6 of Example 1) with 100% ee and a diastereomeric ratio higher than 99.9:0.1. The resulting salt 13 was dissolved under stirring in a mixture of water (34 mL) and 2-methyltetrahydrofuran (24 mL) at 25° C., then HCl 36% (826 mg, 8.15 mmol) was added dropwise, monitoring that internal temperature did not exceed 30° C. The mixture was maintained under the same conditions for 1 hour then stirring was stopped and the ensuing phases separated. The organic layer was washed with water and used without further purification in the following Example.

Example 4

Preparation of (2S,3R)-2-amino-3-(3,4-dihydroxy-phenyl)-3-hydroxypropanoic Acid, i.e. Droxidopa This example is representative of step c.ii.3) of the process of the invention.

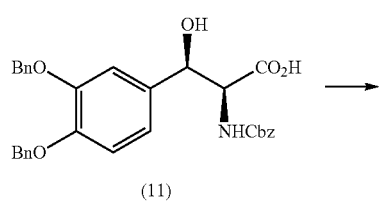

(11)

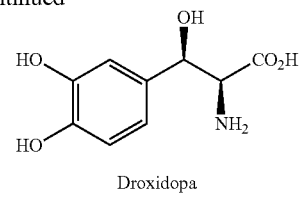

Droxidopa

To the organic layer prepared as described in Example 3 (7.6 mmol theoretical), water (15 mL) and HCl 36% (1.70 g, 16.8 mmol) were added. The resulting biphasic mixture was subjected to 3 cycles of vacuum/nitrogen, then Pd/C 10%, 50% wet w/w (32 mg, 0.015 mmol) was added. The mixture was subjected to 3 cycles of vacuum/hydrogen then pressurized with hydrogen (2 bar) and maintained under stirring at 25° C. for 12 hours.

When the conversion was complete, ascorbic acid (80 mg, 0.46 mmol) was added, the suspension filtered to remove the catalyst, the layers separated and the resulting organic phase washed with water. To the organic phase maintained under stirring a 5% aqueous solution of sodium hydroxide was added dropwise until a pH of 5.0±0.1 was obtained (determined by means of a pHmeter), monitoring that internal temperature did not exceed 30° C. The suspension was cooled to 0° C., filtered and washed with water. To the wet solid, ascorbic acid (80 mg, 0.46 mmol) and water (5 mL) were added and the resulting mixture was maintained under stirring for 1 hour, then filtered and washed with water. The recovered solid was dried under reduced pressure at 50° C. to yield 1.4 g of Droxidopa (86% yield from salt 13) with 100% ee and a diastereomeric ratio higher than 99.9:0.1.

Example 5

Preparation of ethyl 2-isocyanoacetate, Compound of Formula (V) wherein $R^2$ is Ethyl This example is representative of steps d.1) and d.2) of the process of the invention.

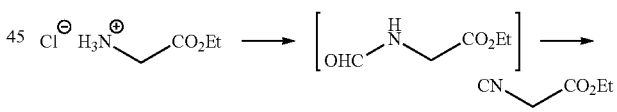

To a suspension of glycine ethyl ester hydrochloride (1.63 g, 11.7 mmol) in ethyl formate (8 mL), triethylamine (1.31 g, 13.0 mmol) was added under stirring. The mixture was heated to reflux and maintained under the same conditions until complete conversion (about 20 hours). The reaction was cooled to 25° C., filtered under nitrogen atmosphere and washed with ethyl formate. The solution was concentrated under reduced pressure to a residue, which was dissolved in dichloromethane (6 mL). Ethyl diisopropylamine (4.0 g, 31.1 mmol) was added and to the resulting solution, cooled to −10° C., and phosphorous oxychloride (1.9 g, 12.3 mmol) was added dropwise monitoring that internal temperature did not exceed 0° C. The mixture was stirred under the same conditions until complete conversion (about 2 hours) then it was slowly poured in a 10% aqueous solution of sodium carbonate monitoring that internal temperature did not exceed 30° C. The resulting phases were separated and the aqueous layer was extracted with dichloromethane (DCM).

The collected organic phases were filtered on a pad of charcoal and celite and analysed according to the following GC method;

GC Method: Column: DB 200, 30 m×320 μm×1.0 μm; Injector temp: 270° C.;

Detector temp: 340° C.; Flow: 5.5 mL/min; Constant pressure: 20.0 psi; Oven:
° C. for 5 min, from 40 to 220° C. at 10° C./min, from 220 to 330 at 30° C./min;

Run time: 60.67 min; Split ratio: 10:1; Injection Volume: 0.5 μL

Rt N-formylglycine ethyl ester: 13.3 min,
Rt ethyl 2-isocyanoacetate: 8.8 min,
Rt glycine ethyl ester: 5.9 min.

The DCM solution containing ethyl 2-isocyanoacetate (about 15 mL) is used as such in the aldol reaction with 3,4-dibenzyloxybenzaldehyde 6 as described in the following Example.

Example 6

Preparation of (2S,3R)-2-amino-3-(3,4-bis(benzyloxy)phenyl)-3-hydroxypropanoic Acid, Compound of Formula (III) wherein $R^1$ is Phenyl This example is representative of operations a) and b) of the process of the invention.

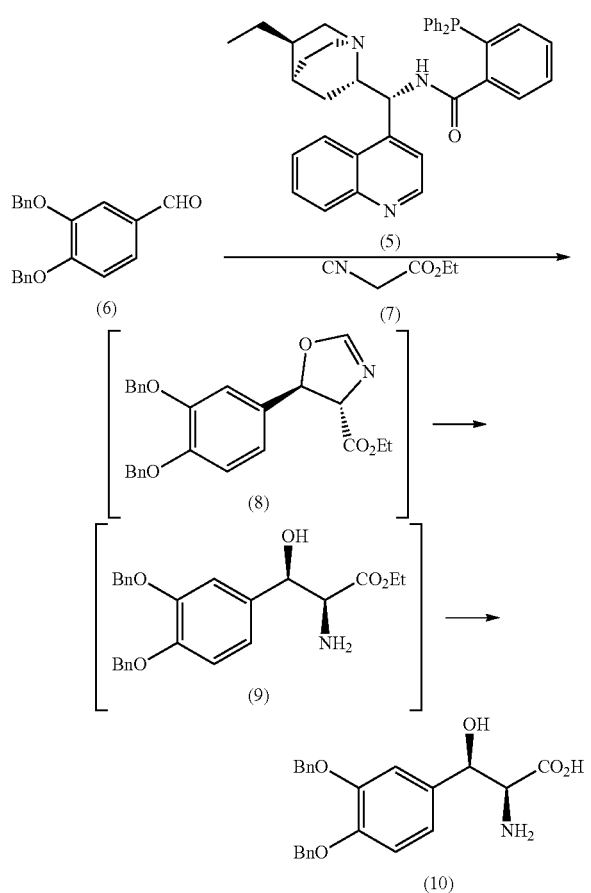

A 10 mL test tube was charged with 3,4-dibenzyloxybenzaldehyde 6 (2.70 g, 8.48 mmol) and compound 5 (100 mg, 0.17 mmol, 2 mol %). Iso-propyl acetate was added (23 mL) followed after 30 min by $Ag_2O$ (10.0 mg, 0.34 mmol, 0.5 mol %). The mixture was stirred at 20° C. for 1 hour, then the solution of ethyl isocyanoacetate 7 (11.7 mmol theoretical) prepared as described in example 5 was added dropwise, monitoring that the internal temperature did not exceed 25° C. The reaction was stirred at the same temperature for 2 hours monitoring periodically by TLC (AcOEt/Hexane 4:6, UV and molibdic) until disappearance of the aldehyde 6.

The mixture was filtered on a celite pad and the filtrate concentrated to a residue. Residual solvents were co-evaporated by stripping with THF. To the crude oxazoline 8 (8.48 mmol theoretical) dissolved in THF (16 mL), 18% HCl (4.64 g, 22.9 mmol) was added. The mixture was stirred at 50° C. for 2 hours, monitoring periodically by TLC (AcOEt/Hexane 4:6 and 100% AcOEt, UV and molibdic) until disappearance of the oxazoline 8 and of the corresponding N-formyl compound.

When the conversion was complete, the mixture was cooled to −5° C. and NaOH (22.4 g, 56.0 mmol) was slowly added monitoring that the internal temperature did not exceed 0° C. The mixture was maintained under stirring at 0° C. for 2 hours then warmed to 25° C. and stirred at the same temperature overnight. The pH was adjusted to 4-5 by addition of acetic acid whereupon precipitation of the amino acid occurred. The mixture was heated to 50° C. in order to observe a clear separation of the phases; the organic layer was separated and used as is in the following Example.

Example 7

(2S,3R)-2-amino-3-(3,4-bis(benzyloxy)phenyl)-3-hydroxypropanoic Acid, Compound of Formula (XI) wherein $R^1$ is Phenyl and Pg is Benzyloxycarbonyl This example is representative of step c.ii.1) of the process of the invention.

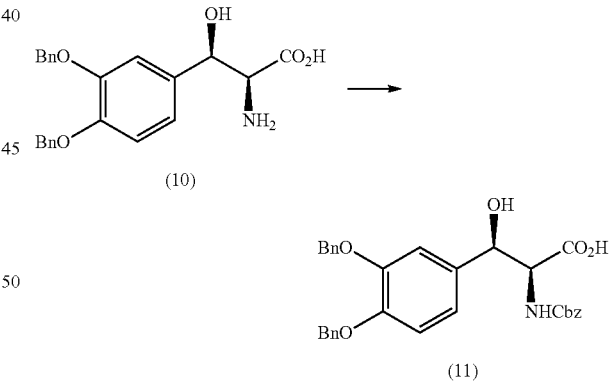

To the organic layer prepared as described in Example 6 (8.48 mmol theoretical), ethyl diisopropylamine was added (1.90 mL, 11.0 mmol) at 20° C. followed by Cbz-OSu (2.32 g, 9.33 mmol) and the reaction was stirred at 25° C. for 1 hour. When the reaction was complete, pH was adjusted to 4-5 by adding acetic acid (0.7 mL) and water (8 mL). THF was removed under reduced pressure and the residue stripped with iso-propyl acetate. The product was extracted with iso-propyl acetate, the combined organic layers were washed with water and concentrated to a residue.

An aliquot of the residue was converted into Droxidopa as described in example 4 and analysed by HPLC according to the method described in the *Journal of Chromatography A* 1994; 675: 244-247 showing a diastereomeric ratio of 90:10 and an enantiomeric ratio 88:12 (ee=76%).

Examples 8A-8G

The aldol reaction described in Example 1 was repeated at different temperatures. After conversion of the oxazoline 8 into the protected amino acid 11, through the amino acid 10, the resulting diastereomeric ratios (d.r.), enantiomeric ratios (e.r.), and ee, determined as described in example 2, were measured. The results of these tests are summarized in Table 1.

TABLE 1

| Example | 8A | 8B | 8C | 8D | 8E | 8F | 8G |
|---|---|---|---|---|---|---|---|
| Temperature (° C.) | 10 | 40 | 60 | 80 | 0 | −20 | −25 |
| d.r. | 90:10 | 91:9 | 90:10 | 90:10 | 91:9 | 89:11 | 90:10 |
| e.r. | 85:15 | 87:13 | 87:13 | 86:14 | 85:15 | 83:17 | 84:16 |
| e.e. (%) | 70 | 74 | 74 | 72 | 70 | 66 | 68 |

Examples 9A-9H

The aldol reaction described in Example 1 was repeated using catalytic systems with different molar amounts of compound 5 and $Ag_2O$ with respect to 3,4-dibenzyloxybenzaldehyde 6. After conversion of the oxazoline 8 into the protected amino acid 11, through the amino acid 10, the resulting diastereomeric ratios (d.r.), enantiomeric ratios (e.r.), and ee, determined as described in example 2, were measured. The results of these tests are summarized in Table 2.

TABLE 2

| Example | 9A | 9B | 9C | 9D | 9E | 9F | 9G | 9H |
|---|---|---|---|---|---|---|---|---|
| Molar ratio comp. 5/ comp. 6 (%) | 1.6 | 1.2 | 0.8 | 0.4 | 0.5 | 1.0 | 3.0 | 4.0 |
| Molar ratio $Ag_2O$/ comp. 6 (%) | 0.4 | 0.3 | 0.2 | 0.1 | 0.5 | 0.5 | 0.5 | 0.5 |
| d.r. | 90:10 | 90:10 | 90:10 | 85:11 | 85:11 | 85:11 | 85:11 | 85:11 |
| e.r. | 85:15 | 85:15 | 84:16 | 81:19 | 81:19 | 81:19 | 81:19 | 81:19 |
| e.e. (%) | 70 | 70 | 68 | 62 | 62 | 62 | 62 | 62 |

Example 10

The aldol reaction described in example 1 was repeated using a catalytic system comprising a compound 14 instead of the reported compound 5. After conversion of the oxazoline 8 into the protected amino acid 11, through the amino acid 10, the resulting diastereomeric and enantiomeric ratio, determined as described in example 2, were respectively 91:9 and 89:11 (ee=78%).

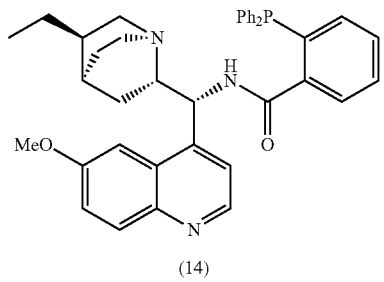

(14)

Example 11

The aldol reaction described in example 1 was repeated using a catalytic system comprising only $Ag_2O$ instead of the reported mixture of $Ag_2O$ and compound 5. After conversion of the oxazoline 8 into the protected amino acid 11, through the amino acid 10, the resulting diastereomeric and enantiomeric ratio, determined as described in example 2, were respectively 75:25 and 50:50 (ee=0%).

Example 12

The aldol reaction described in example 1 was repeated using a catalytic system comprising only compound 5 instead of the reported mixture of $Ag_2O$ and compound 5. After 12 hours no conversion of 3,4-dibenzyloxybenzaldehyde 6 into oxazoline 8 was observed.

Example 13

The aldol reaction described in example 1 was repeated using a catalytic system comprising CuCl instead of the reported $Ag_2O$. After conversion of the oxazoline 8 into the protected amino acid 11, through the amino acid 10, the resulting diastereomeric and enantiomeric ratio, determined as described in example 2, were respectively 68:32 and 50:50 (ee=0%).

Example 14

The aldol reaction described in example 1 was repeated adding powdered 4 A molecular sieves to the mixture of aldehyde 6 and compound 5 and $Ag_2O$ in iso-propyl acetate. After conversion of the oxazoline 8 into the protected amino acid 11, through the amino acid 10, the resulting diastereomeric and enantiomeric ratio, determined as described in example 2, were respectively 90:10 and 87:13 (ee=74%).

Example 15

Preparation of (2S,3R)-2-amino-3-(3,4-bis(benzyloxy)phenyl)-3-hydroxypropanoic Acid, Compound of Formula (III) Wherein $R^1$ is Phenyl This example is representative of operations a) and b) of the process of the invention.

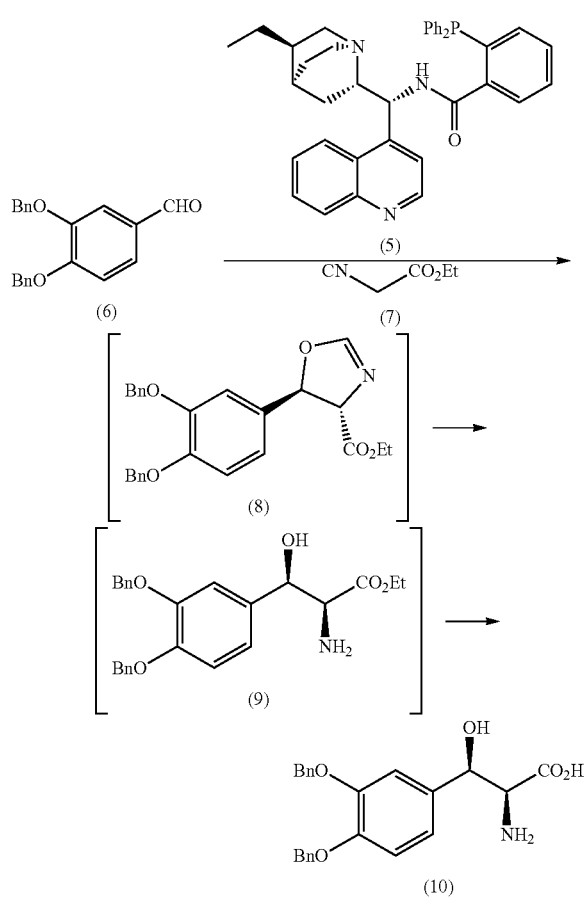

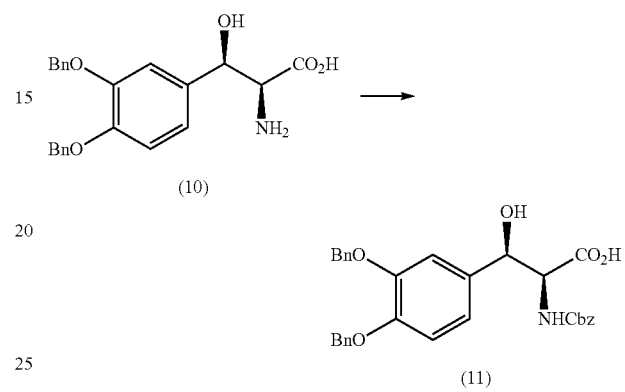

A 10 mL test tube was charged with 3,4-dibenzyloxybenzaldehyde 6 (0.271 g, 0.85 mmol) and compound 5 (0.025 g, 5 mol %). Iso-propyl acetate was added (2.8 mL) and the mixture was stirred at 20° C. for 10 minutes. Then it was cooled to −20° C. and Ag$_2$O (0.005 g, 2.5 mol %) was added. The mixture was stirred at the same temperature for 20 minutes, then ethyl isocyanoacetate 7 (0.101 g, 0.89 mmol) was added dropwise. The reaction was stirred at the same temperature for 10 hours monitoring periodically by TLC (AcOEt/Hexane 4:6, UV and molibdic) until disappearance of the aldehyde 6.

The mixture was filtered on a HPLC filter and the filtrate concentrated to a residue.

Crude oxazoline 8 (0.85 mmol theoretical) was dissolved in THF (3.7 mL) and 6N HCl (0.38 mL, 2.30 mmol). The mixture was stirred at 50° C. for 2 hours, monitoring periodically by TLC (AcOEt/Hexane 4:6 and 100% AcOEt, UV and molibdic) until disappearance of the oxazoline 8 and of the corresponding N-formyl compound.

When the conversion was complete, the mixture was cooled to 0° C. and 2N NaOH (2.8 mL, 5.64 mm) was added dropwise monitoring that the internal temperature did not exceed 10° C. The mixture was then warmed to 25° C. and stirred at the same temperature overnight. The pH was adjusted to 5 by addition of acetic acid whereupon precipitation of the amino acid occurred. The mixture was heated to 50° C. in order to observe a clear separation of the phases; the organic layer was separated and used as is in the following Example.

Example 16

Preparation of (2S,3R)-2-amino-3-(3,4-bis(benzyloxy)phenyl)-3-hydroxypropanoic Acid, Compound of Formula (XI) wherein $R^1$ is Phenyl and Pg is Benzyloxycarbonyl This example is representative of step c.ii.1) of the process of the invention.

To the organic layer prepared as described in Example 15 (0.85 mmol theoretical), ethyl diisopropylamine was added (0.223 mL, 1.28 mmol) at 0° C. followed by Cbz-OSu (0.234 g, 0.94 mmol) and the reaction was stirred at 25° C. for 1 hour. When the reaction was complete the pH was adjusted to about 5 by addition of a mixture of acetic acid (0.1 mL) and water (1.0 mL). THF was removed under reduced pressure and the product extracted with iso-propyl acetate. The combined organic layers were washed with water and concentrated to a residue.

An aliquot of the residue was converted into Droxidopa as described in example 4 and analysed by HPLC according to the method described in the *Journal of Chromatography A* 1994; 675: 244-247 showing a diastereomeric ratio of 91:9 and an enantiomeric ratio 84:16 (ee=68%).

Examples 17A-17F

The aldol reaction described in Example 15 was repeated using different solvents in place of the reported iso-propyl acetate.

After conversion of the oxazoline 8 into the protected amino acid 11, through the amino acid 10, the resulting diastereomeric ratios (d.r.), enantiomeric ratios (e.r.), and ee, determined as described in Example 16, were measured. The results of these tests are summarized in Table 3; in the first column, it is reported the specific solvent tested in each Example.

TABLE 3

| Example | Solvent | d.r. | e.r. | e.e. (%) |
|---|---|---|---|---|
| 17A | Ethyl acetate | 90:10 | 84:16 | 68 |
| 17B | Acetonitrile | 85:15 | 80:20 | 60 |
| 17C | Methyl tert-butyl ether | 90:10 | 81:19 | 62 |
| 17D | Cyclopentyl methyl ether | 90:10 | 80:20 | 60 |
| 17E | Tetrahydrofuran | 86:14 | 84:16 | 68 |
| 17F | 2-methyl tetrahydrofuran | 87:13 | 86:14 | 72 |

Example 18

The aldol reaction described in Example 8E was repeated using tert-butyl isocyanoacetate instead of the reported ethyl isocyanoacetate. After conversion of the oxazoline 8 into the protected amino acid 11, through the amino acid 10, the resulting diastereomeric and enantiomeric ratio, determined as described in Example 16, were respectively 93:7 and 92:8 (ee=84%).

Example 19

The aldol reaction described in example 1 was repeated using a catalytic system comprising a 85:15 mixture of compounds 15 and 14 instead of the reported compound 5. After conversion of the oxazoline 8 into the protected amino acid 11, through the amino acid 10, the resulting diastereomeric and enantiomeric ratio, determined as described in example 2, were respectively 91:9 and 88:12 (ee=76%).

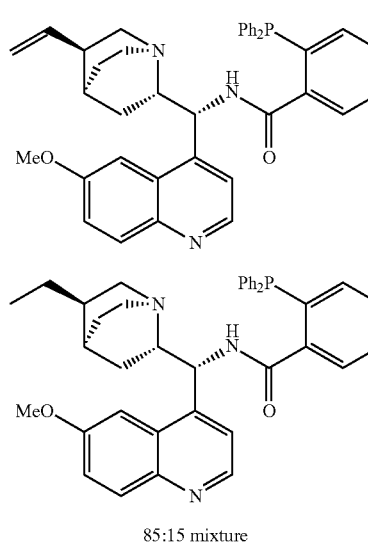

85:15 mixture

Example 20

The aldol reaction described in example 8B was repeated using a catalytic system comprising a 85:15 mixture of compounds 15 and 14 instead of the reported compound 5. After conversion of the oxazoline 8 into the protected amino acid 11, through the amino acid 10, the resulting diastereomeric and enantiomeric ratio, determined as described in example 2, were respectively 92:8 and 90:10 (ee=80%).

Example 21

The aldol reaction described in Example 20 was repeated using tert-butyl isocyanoacetate instead of the reported ethyl isocyanoacetate. After conversion of the oxazoline 8 into the protected amino acid 11, through the amino acid 10, the resulting diastereomeric and enantiomeric ratio, determined as described in Example 16, were respectively 96:4 and 95:5 (ee=90%).

The invention claimed is:

1. A process for the preparation of a diastereomerically and enantiomerically pure mixture of an amino acid of general formula (IV) or a salt thereof:

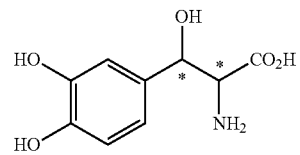

said process comprising the following synthetic operations:

a) preparing a diastereomerically and enantiomerically enriched mixture of the oxazoline of general formula (II) by reacting a benzaldehyde (I) with an isocyanoacetate (V) in the presence of a catalytic system comprising a 9-amino(9-deoxy)epi Cinchona alkaloid derivative (VIII) and a salt of silver or gold or a mixture thereof:

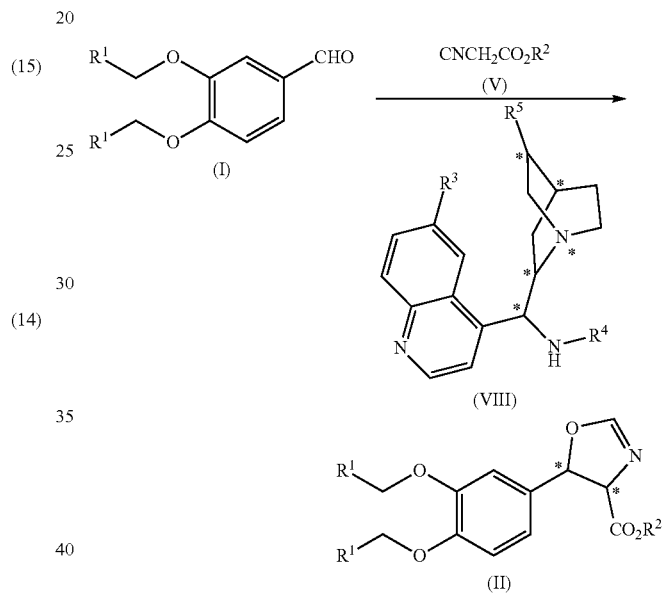

wherein:

$R^1$ is a C6-C10 aryl or a substituted C6-C10 aryl;

$R^2$ is a C1-C6 linear or branched alkyl, a C6-C10 aryl or a C1-C6 linear or branched alkyl substituted with a C6-C10 aryl;

$R^3$ is H, OH, or a C1-C6 linear or branched alkoxy;

$R^4$ is

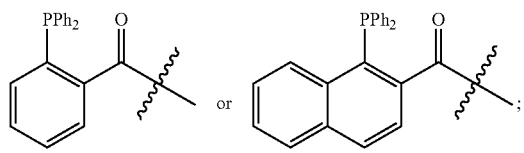

and $R^5$ is an ethyl or a vinyl group;

b) converting said enriched mixture of the oxazoline of general formula (II) into a diastereomerically and enantiomerically enriched mixture of the protected amino acid of general formula (III):

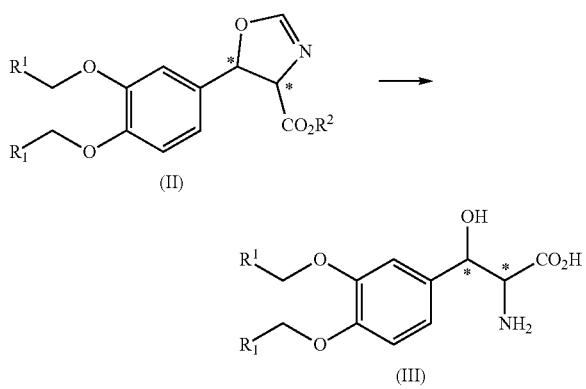

c) converting the enriched mixture of the protected amino acid of general formula (III) into a diastereomerically and enantiomerically pure mixture of the amino acid of general formula (IV):

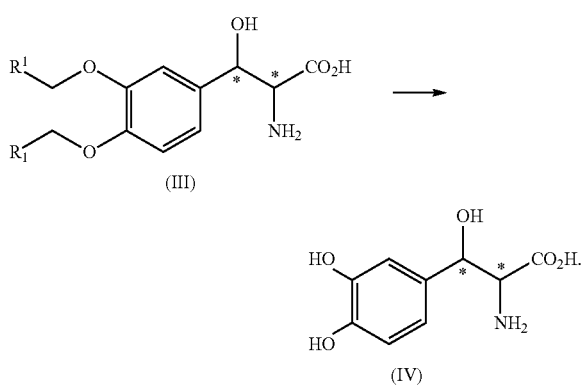

2. The process according to claim 1, in which said 9-amino(9-deoxy)epi Cinchona alkaloid derivative is selected among a compound of formula (VIIIA) or (VIIIB):

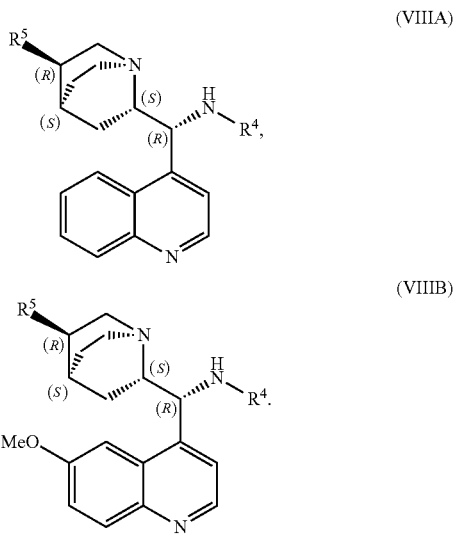

3. The process according to claim 1, in which a mixture of unsaturated/saturated 9-amino(9-deoxy)epi Cinchona alkaloid derivatives, as shown below, is used in the reaction of operation a)

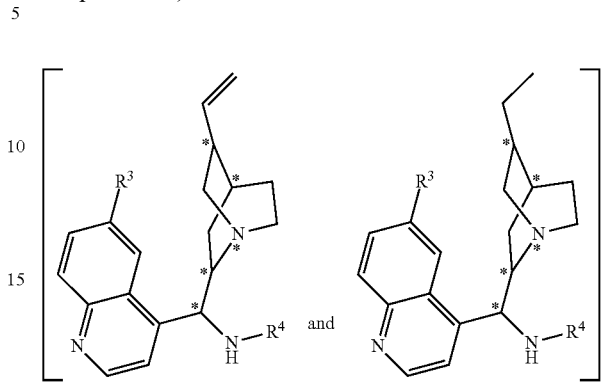

4. The process according to claim 1, in which said salts of silver or gold are selected among silver acetate, silver carbonate, silver oxide, chloro(triphenylphosphine)gold or a mixture thereof.

5. The process according to claim 1, in which the amount of isocyanoacetate (V) is between 1 and 1.5 equivalents with respect to the amount of benzaldehyde (I) used.

6. The process according to claim 1, in which the molar amount of the 9-amino(9-deoxy)epi Cinchona alkaloid derivative is between 1/200 and 1/20 with respect to the amount of benzaldehyde of general formula (I) used.

7. The process according to claim 1, in which the molar amount of said salt of silver or gold or of the mixture thereof with respect to the 9-amino(9-deoxy)epi Cinchona alkaloid derivative in the catalytic system is between 1:1 and 1:8 (mol/mol).

8. The process according to claim 1, in which operation b) comprises the following steps:

b.1) converting the enriched mixture of the oxazoline of general formula (II) prepared in operation a) into the corresponding enriched mixture of N-formyl derivative (IX):

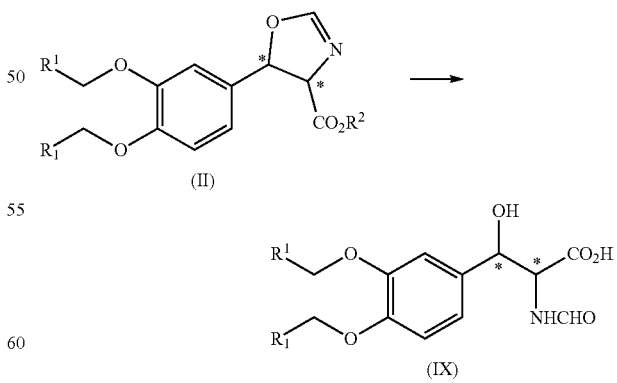

b.2) converting said enriched mixture of N-formyl derivative (IX) into a diastereomerically and enantiomerically enriched mixture of the protected amino acid of general formula (III):

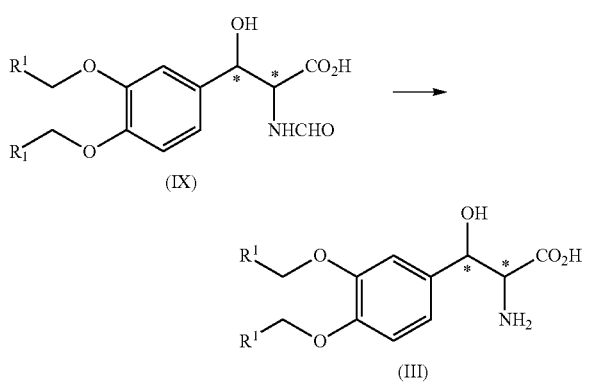

wherein $R^1$ and $R^2$ have the meanings given above.

9. The process according to claim 8, in which the ester moiety of N-formyl derivative (IX) is hydrolyzed under acid or basic conditions.

10. The process according to claim 1, in which operation c) is carried out according to a first alternative route of synthesis c.i), comprising the following steps:

c.i.1) converting the enriched mixture of the protected amino acid of general formula (III) prepared in operation b) into a diastereomerically and enantiomerically enriched mixture of the amino acid of general formula (IV):

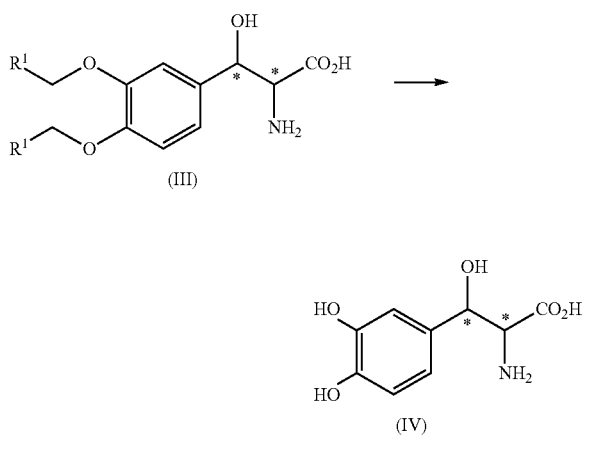

wherein $R^1$ has the meanings given above;

c.i.2) converting the enriched mixture of the amino acid of general formula (IV) into a diastereomerically and enantiomerically pure mixture thereof by crystallization of a supersaturated solution of said enriched mixture (IV) in water or in a mixture of water and a water-miscible solvent.

11. The process according to claim 1, in which operation c) is carried out according to a second alternative route of synthesis c.ii), comprising the following steps:

c.ii.1) protecting the amino group of the diastereomerically and enantiomerically enriched mixture of the protected amino acid of general formula (III) prepared in operation b), producing an enriched mixture of the protected amino acid of general formula (XI):

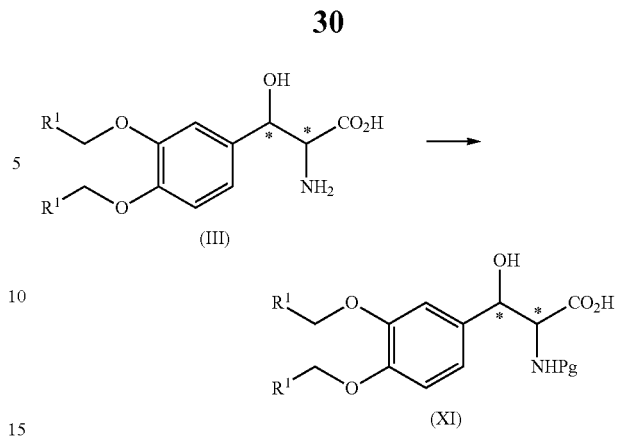

c.ii.2) converting said enriched mixture of the protected amino acid of general formula (XI) into a diastereomerically and enantiomerically pure mixture of the protected amino acid of general formula (XII):

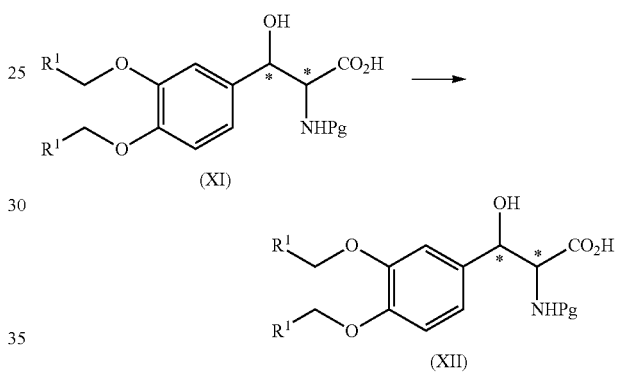

c.ii.3) converting the pure mixture of the protected amino acid of general formula (XII) into a diastereomerically and enantiomerically pure mixture of the amino acid of general formula (IV):

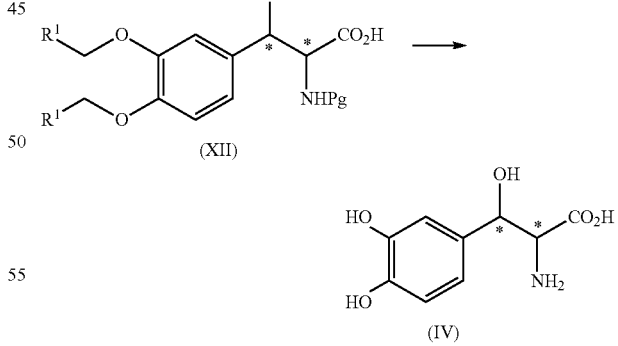

wherein:
$R^1$ has the meanings given above; and
Pg is a nitrogen protecting group.

12. The process according to claim 11, in which step c.ii.2) is carried out by treating said enriched mixture of the protected amino acid of general formula (XI), optionally isolated, with an optically active amine to obtain the corresponding salt, followed by diastereomeric salt resolution of the two enantiomers of the threo product and de-blocking of the diastereomerically and enantiomerically pure mixture by treatment with an acid.

13. The process according to claim 1, wherein in operation a) the 9-amino(9-deoxy)epi Cinchona alkaloid derivative (VIII) is a compound of formula (VIIIC)

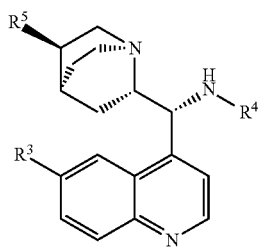

(VIIIC)

wherein $R^3$, $R^4$ and $R^5$ are as defined in claim 1, and the diastereomerically and enantiomerically enriched mixture of the oxazoline of general formula (II) is an enantiomerically enriched trans-oxazoline of general formula (IIA):

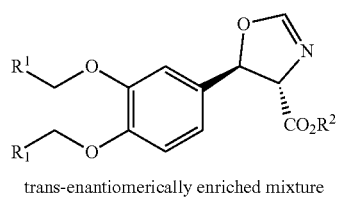

(IIA)

trans-enantiomerically enriched mixture and the process leads to the formation of an enantiomerically pure threo-amino acid of general formula (IVA):

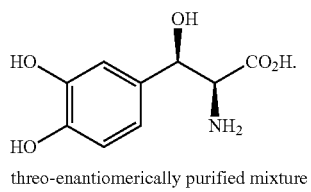

(IVA)

threo-enantiomerically purified mixture

14. The process according to claim 1, further comprising a preliminary operation d) of preparation of the isocyanoacetates (V) for use in operation a), said operation d) comprising the following steps:
   d.1) converting a glycine derivative of formula (VI) or a salt thereof, by treatment with a formate, into the corresponding N-formyl derivative (VII):

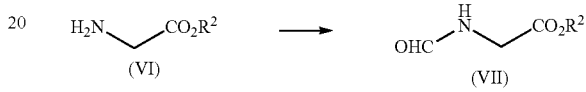

d.2) dehydrating said N-formyl derivative (VII) to obtain an isocyanoacetate (V):

wherein $R^2$ is a C1-C6 linear or branched alkyl, a C6-C10 aryl, or a C1-C6 linear or branched alkyl substituted with a C6-C10 aryl.

15. The process according to claim 14, in which the solution resulting from step d.2) is used as such in the reaction of operation a).

* * * * *